United States Patent
Falahee

(10) Patent No.: US 7,674,297 B2
(45) Date of Patent: Mar. 9, 2010

(54) ANATOMIC VERTEBRAL CAGE

(75) Inventor: Mark H. Falahee, Ann Arbor, MI (US)

(73) Assignee: U.S. Spinal Technologies, LLC, Boca Raton, FL (US)

( * ) Notice: Subject to any disclaimer, the term of this patent is extended or adjusted under 35 U.S.C. 154(b) by 1357 days.

(21) Appl. No.: 10/462,498

(22) Filed: Jun. 16, 2003

(65) Prior Publication Data
US 2004/0034430 A1 Feb. 19, 2004

Related U.S. Application Data

(60) Provisional application No. 60/388,974, filed on Jun. 14, 2002.

(51) Int. Cl.
A61F 2/44 (2006.01)
(52) U.S. Cl. .................. 623/17.16; 623/17.11
(58) Field of Classification Search .................. 606/61; 623/17.11, 17.16
See application file for complete search history.

(56) References Cited

U.S. PATENT DOCUMENTS

| | | | | |
|---|---|---|---|---|
| 3,867,728 A | * | 2/1975 | Stubstad et al. | 623/17.16 |
| 3,941,127 A | * | 3/1976 | Froning | 604/506 |
| 4,501,269 A | | 2/1985 | Bagby | 128/95 G |
| 5,397,364 A | * | 3/1995 | Kozak et al. | 623/17.11 |
| 5,609,635 A | * | 3/1997 | Michelson | 623/17.16 |
| 5,669,909 A | * | 9/1997 | Zdeblick et al. | 606/61 |
| 5,683,394 A | * | 11/1997 | Rinner | 606/86 |
| 5,766,252 A | * | 6/1998 | Henry et al. | 623/17.16 |
| 6,033,405 A | * | 3/2000 | Winslow et al. | 606/61 |
| 6,159,211 A | * | 12/2000 | Boriani et al. | 606/61 |
| 6,425,920 B1 | * | 7/2002 | Hamada | 623/17.16 |
| 6,964,687 B1 | * | 11/2005 | Bernard et al. | 623/17.16 |
| 2001/0012966 A1 | * | 8/2001 | Studer et al. | 623/17.16 |
| 2002/0068977 A1 | * | 6/2002 | Jackson | 623/17.15 |
| 2004/0126407 A1 | * | 7/2004 | Falahee | 424/423 |

FOREIGN PATENT DOCUMENTS

WO    WO 01/03615 A1  *  1/2001

* cited by examiner

*Primary Examiner*—Paul Prebilic
(74) *Attorney, Agent, or Firm*—Gifford, Krass, Sprinkle, Anderson & Citkowski, P.C.

(57) ABSTRACT

A spinal fusion system includes a cage with a fillable volume and removable locking gate, thereby enabling the fillable volume to be packed with graft, biologic or other materials prior to the gate being closed and locked. In the preferred embodiment, the locking gate is positioned anteriorly, though lateral, posterior, and combinations thereof are also possible. The cage is preferably radiolucent, being composed of a carbon fiber, but with one or more radiopaque markers to provide a certain degree of visualization. Some or all of the walls of the cage may include superior and/or inferior surface features to enhance positioning and/or minimize back-out, and the posterior wall may be indented to prevent neurocompression. The sidewalls of the cage may further include a recessed face with nipple indents and locking fasteners. According to a system aspect of the invention, multiple cages are provided, each being shaped differently for use at different spinal levels. For example, the cage may be larger and more trapezoidally-pronounced for the L5-S1 levels, or smaller and less trapezoidally pronounced for the T and L2 levels. The system may further including an implant introducer instrument geometrically matched to the cage, and the matched implant introducer instruments and cages may be color-coded to expedite the procedure.

2 Claims, 4 Drawing Sheets

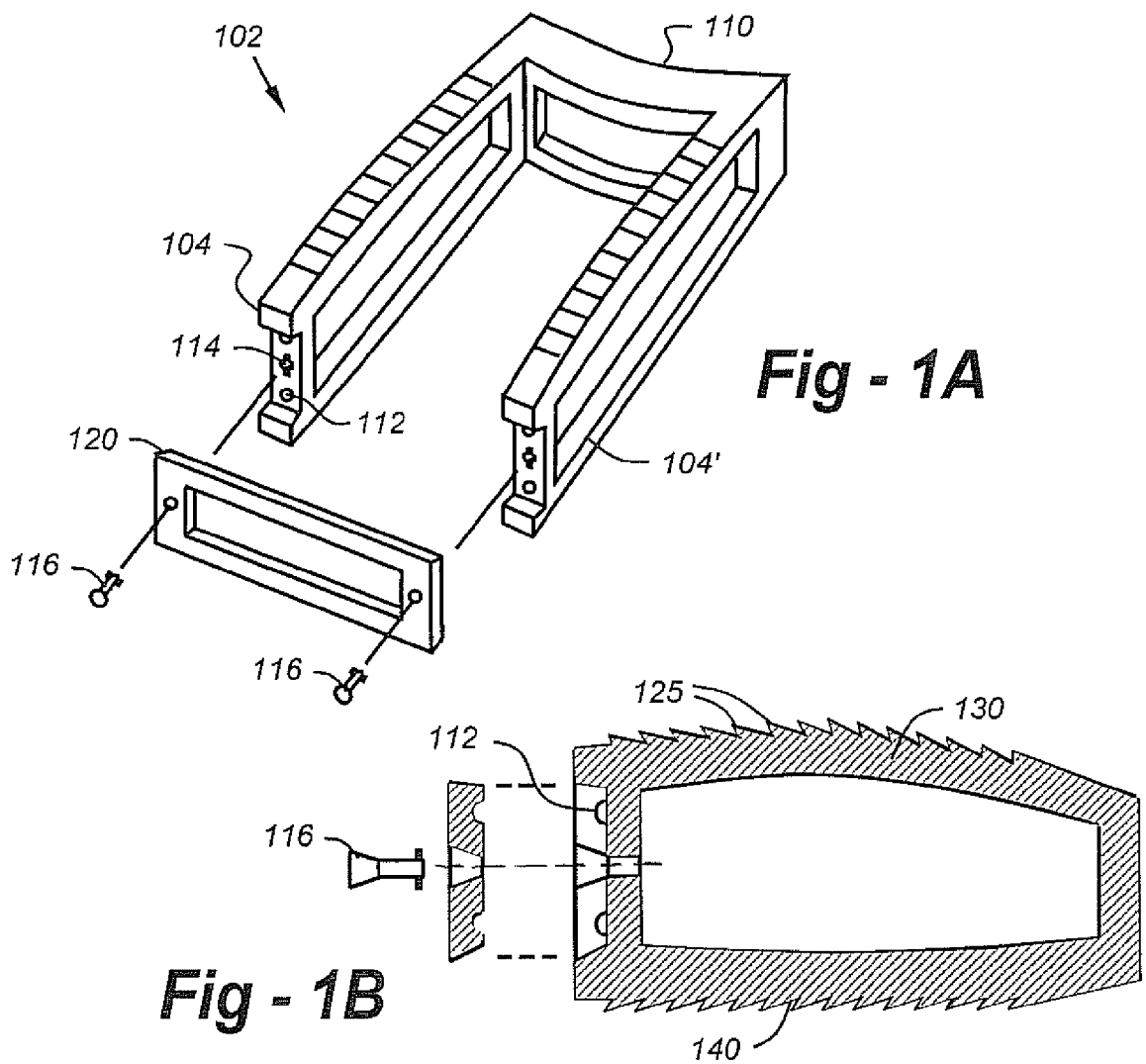
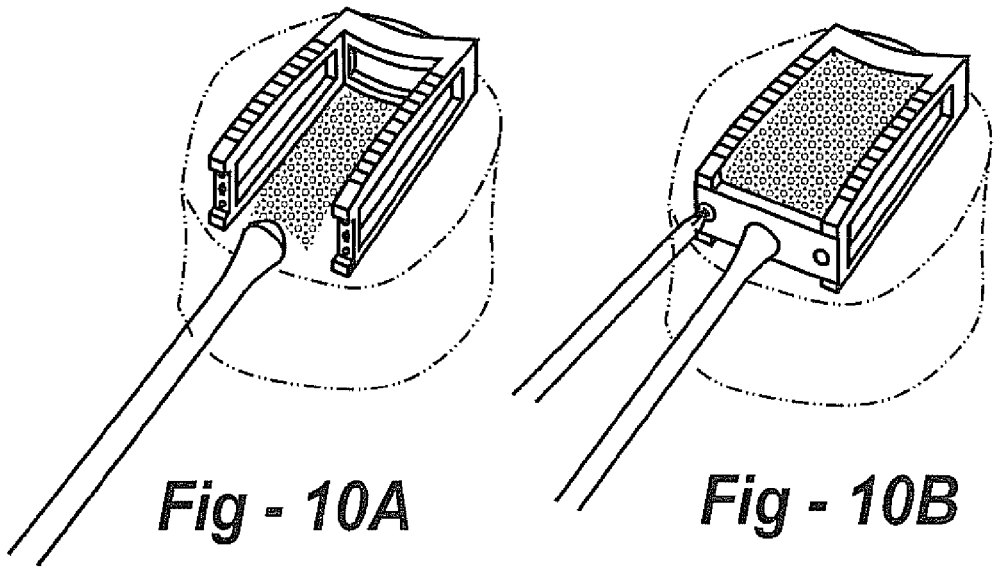

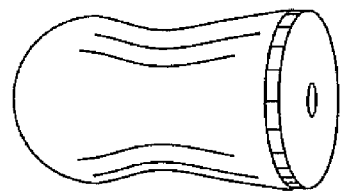
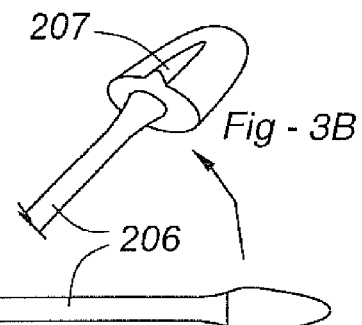
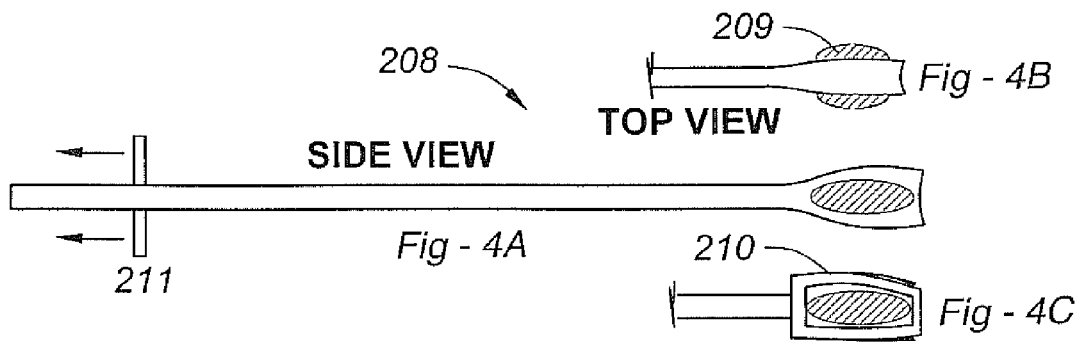
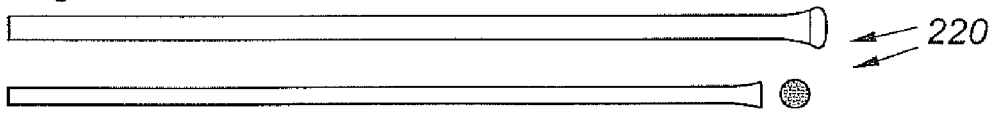
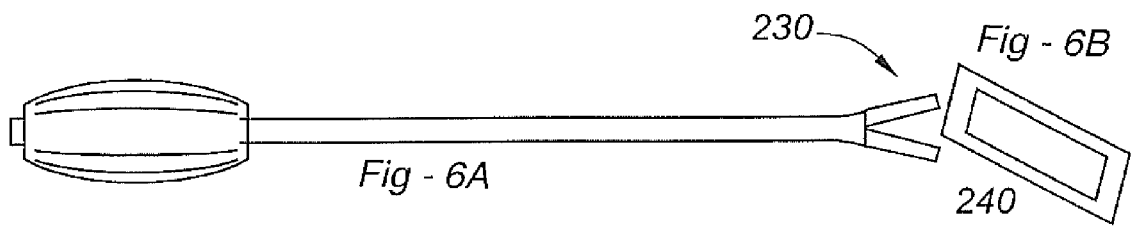

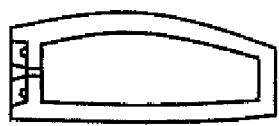  
*Fig – 8A*  *Fig – 8B*  *Fig – 8C*
 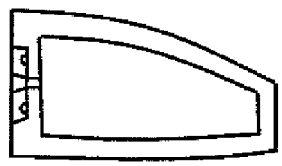 
*Fig – 8D*  *Fig – 8E*  *Fig – 8F*
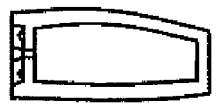  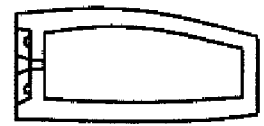
*Fig – 8G*  *Fig – 8H*  *Fig – 8I*

ANATOMIC VERTEBRAL CAGE

REFERENCE TO RELATED APPLICATION

This application claims priority from U.S. Provisional Patent Application Ser. No. 60/388,974, filed Jun. 14, 2002, the entire content of which is incorporated herein by reference.

FIELD OF THE INVENTION

This invention relates generally to spinal fusion and, in particular, to an anatomic, fillable cage and instrumentation therefore.

BACKGROUND OF THE INVENTION

There are many surgical approaches and methods used to fuse the spine. Most involve the placement of a bone graft between the vertebrae. Supplemental hardware, such as plates, screws and cages may or may not be used, depending upon the indication.

An early cage design is described in U.S. Pat. No. 4,501,269 to Bagby, entitled "PROCESS FOR FUSING BONE JOINTS." According to the method, a hole is bored transversely across the joint and a slightly larger cylindrical basket is driven into the hole, thereby spreading the bones in resistance to the tensile forces of the surrounding tissue. Immediate stabilization of the joint is achieved by the implantation of the rigid cylindrical basket. Subsequent bone-to-bone fusion is achieved, both through and about the basket, which is filled with bone fragments produced during the boring step.

The Bagby patent states that the process is applicable to any human or animal joint formed by opposed contiguous bony surfaces which are covered and separated by intervening cartilage and are surrounded by ligaments which resist expansion of the joint. Specific examples of such joints are a spinal joint between adjacent vertebrae or the ankle joint. This stand-alone interbody fusion technique continued to evolve with material changes and the design of threaded cages to increase stability and decrease displacement rates. Bilateral, parallel implants were designed for use in the lumbar spine, with the first human implantation occurring in the early 1009s. The cylindrical titanium cages were threaded to screw into the endplates, thereby stabilizing the device and allowing for increased fusion rate with a stand-alone anterior device.

Ray and colleagues developed a similar titanium interbody fusion device which was initially used in posterior lumbar interbody fusions (PLIF), but expanded to include ALIF procedures. In 1985, Otero-Vich reported using threaded bone dowels for anterior cervical arthrodesis, and femoral ring allograft bone has subsequently been fashioned into cylindrical threaded dowels for lumbar application.

Currently, there are a wide number of available interbody fusion devices of varying design and material, including:
1) Cylindrical threaded titanium interbody cages;
2) Cylindrical threaded cortical bone dowels; and
3) Vertical interbody rings, boxes and wedges.

All existing devices are prefabricated and not anatomically shaped, thus requiring the intervertebral space to be shaped to accommodate the device. This requires multiple steps and tools to prepare the area, distract, measure, and trial/size prior to ultimate placement. The requisite distraction devices and trial sizers interfere with the actual device for implant, creating more steps and decreasing the accuracy of placement. Other solutions, such as mesh cages and bone materials, are prone to deformation and/or breakage when attempts are made to force them into the discal interspace.

As a consequence of these limitations, only a small area of the endplate surface remains proximate to bone graft, which is dictated by the size and position of the cage. With current approaches, it is also difficult to visualize bone fusion mass because the cages and other devices are metal, and large trays are required with many instruments, due to the large number of different sized cages.

SUMMARY OF THE INVENTION

This invention improves upon existing solutions by providing a spinal fusion system including a cage with a fillable volume and removable locking gate, thereby enabling the fillable volume to be packed with graft, biologic or other materials prior to the gate being closed and locked. In the preferred embodiment, the locking gate is positioned anteriorally, though lateral, posterior, and combinations thereof are also possible.

The cage is preferably radiolucent, being composed of a carbon fiber, but with one or more radiopaque markers to provide a certain degree of visualization. Some or all of the walls of the cage may include superior and/or inferior surface features to enhance positioning and/or minimize back-out, and the posterior wall may be indented to prevent neurocompression. The sidewalls of the cage may further include a recessed face with nipple indents and locking fasteners.

According to a system aspect of the invention, multiple cages are provided, each being shaped differently for use at different spinal levels. For example, the cage may be larger and more trapezoidally-pronounced for the L5-S1 levels, or smaller and less trapezoidally pronounced for the T and L2 levels. The system may further include an implant introducer instrument geometrically matched to the cage, and the matched implant introducer instruments and cages may be color-coded to expedite the procedure.

BRIEF DESCRIPTION OF THE DRAWINGS

FIGS. 1A and 1B illustrate an intervertebral cage according to the invention including contoured, dome-shaped sidewalls and a flat, trapezoidal under surface;

FIG. 2 is a drawing which shows this detachable ratchet handle;

FIGS. 3A and 3B show contoured wedge-shaped retractors according to the invention;

FIGS. 4A-4C provides different views of the U-cage introducer;

FIGS. 5A and 5B are drawings of a graph impactor;

FIGS. 6A and 6B show a gate holder according to the invention;

FIG. 7 illustrates a screwdriver, attached to the detachable ratchet handle;

FIGS. 8A-8C are side views of cage shapes applicable to L2-L5;

FIGS. 8D-8F illustrate larger, preferably more trapezoidally-shaped devices for L5-S1 levels;

FIGS. 8G-8I show smaller, less trapezoidal and less dome-shaped devices applicable to T and L2 levels;

FIG. 9E, shown from an oblique perspective, illustrates how the endplates are easily accessed according to the invention;

FIG. 10A shows how the endplates are prepared and the space is packed with graph/biologic material, as appropriate; and FIG. 10B shows how a correspondingly sized anterior plate is locked in place using the gate holder and locking screws.

DETAILED DESCRIPTION OF THE INVENTION

Figure 9A:
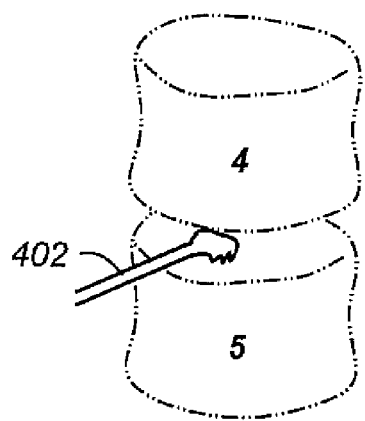
FIG. 9A illustrates the removal of disc material between the L4 and L5 levels.

This invention improves upon the prior art by providing a cage system with significant advantages, independently and in combination. The system is capable of a custom fit while, at the same time, eliminates multiple steps, instruments and trays, and allows easier and greater access to endplate surface area. The invention can be used with autograph, allograph, and/or biologic materials.

In the preferred embodiment, the device according to the invention takes the form of a carbon fiber-faced cage. The structure is generally radiolucent, while including small radiopaque markers to provide some degree of visualization.

In terms of apparatus, the open-face cage 102 preferably includes contoured, dome-shaped sidewalls 104, 104' with a flat, trapezoidal under surface, as shown in FIGS. 1A and 1B. Separate cages are provided along with tools for levels L5 to S1, which typically require a more pronounced trapezoidal shape.

Also in the preferred embodiment, the indented back wall 110 of the cage is indented to prevent neurocompression. The sidewalls also preferably include a recessed face with nipple indents 112 and locking screw holes 114 to receive a locking screw 116. A closing face gate 120 with non-slip nipples and locking screw holes are provided along with fasteners, such as a pair of locking screws.

Thus, in terms of an intermediate summary, some of the unique features of this invention include a cage having dome-shaped contours for the upper endplate, different shapes for the L5-S1 level, an indented back wall and an open face with a closing gate including a locking mechanism. Since it is considered that many, if not all, of these features are independently unique and therefore patentable, this invention anticipates any of these features alone or in combination. The side view in FIG. 1B illustrates the optional use of sawtooth features 125 on the upper surface 130, which is preferably dome-shaped, and the lower surface 140, which is preferably flat.

The invention further includes instrumentation, also considered to represent novel subject matter. A series of contoured, wedge-shaped distracters are provided, preferably including a color-coded centering mark. Separate distracters are used for the trapezoidal-shaped L5 to S1 levels. A correspondingly coded final "U-cage introducer" is included along with ring curettes, claws and endplate prep tools, and the like. Additionally, a graph impactor and gate holder/screwdriver are used, preferably in conjunction with a detachable ratchet handle.

FIG. 2 is a drawing which shows this detachable ratchet handle. FIG. 3A is a drawing which shows contoured wedge-shaped retractors 206, preferably including a color-coded raised centering mark or ridge 207 (shown in FIG. 3B) according to the invention. FIG. 4A is a view of the U-cage introducer 208, preferably including retractable wings 209 (shown in FIG. 4B) to release a cage 210 (shown in FIG. 4C) using control 211. FIGS. 5A and 5B are drawings of a graph impactor 220. FIG. 6A shows a gate holder 230 used to capture and release a gate 240 (shown in FIG. 6B) according to the invention. FIG. 7 illustrates a screwdriver, attached to the detachable ratchet handle which can be used with any of the instruments shown in FIGS. 2-6 as well.

With respect to the implants, and as discussed elsewhere herein, varying sizes of U-shaped cages are provided, which may include crescent-shaped sidewalls, domed tops, and indented back walls. Again, these are composed of carbon fiber with radiopaque markers, and preferably include serrated or tooth-edged endplate surfaces to enhance gripping and to prevent back out. Correspondingly sized anterior gates are provided, also preferably composed of carbon fiber, having non-slip nipples and holes to receive locking fasteners such as screws. FIGS. 8A-8C are side views of shapes applicable to L2-L5. FIGS. 8D-8F illustrate larger, preferably more trapezoidally-shaped devices for L5/S1, and FIGS. 8G-8I show smaller, less trapezoidal and less dome-shaped devices applicable to T and L2 levels.

Figure 9C:
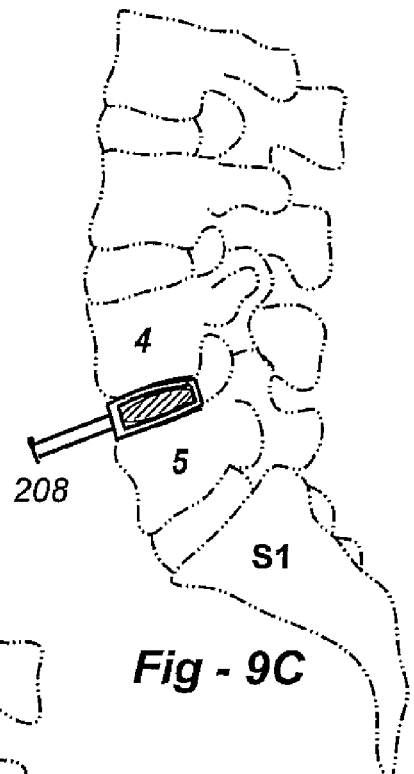
FIGS. 9B and 9C show dilution.
Figure 9D:
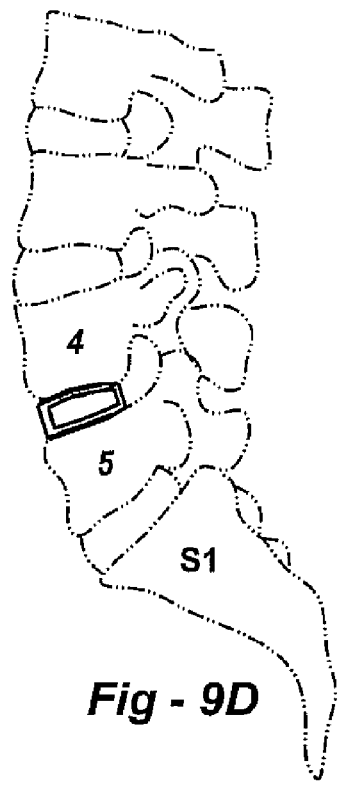
FIGS. 9D and 9E depict cage placement.
Figure 9B:
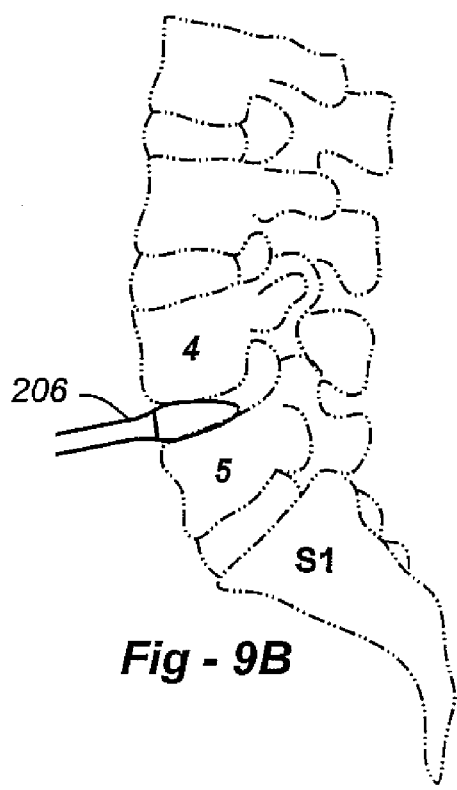
Figure 9E:
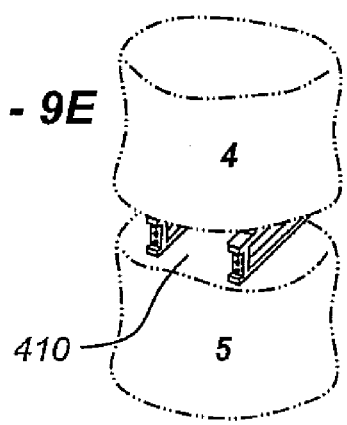

In terms of surgical protocol, an anterior approach is used to access the intervertebral space. Disc material is removed as appropriate, and the lateral extent of the disc space is determined. The disc space is then dilated to an appropriate height utilizing the color-coded distracters according to the invention. Upon removal of the final distracter, it is replaced with the same, color-coded implant introducer instrument. The implant is released and the introducer tool is removed. FIG. 9A illustrates the removal of disc material between the L4 and L5 levels. Dilation is shown as FIG. 9B and cage insertion shown in FIG. 9C. The cage in place is shown in FIGS. 9D and 9E. FIG. 9E, shown from an oblique perspective, illustrates how the endplates are easily accessed according to the invention.

As shown in FIG. 10A, the endplates are prepared and the space is packed with graph/biologic material, as appropriate. A correspondingly sized anterior plate is then locked in place using the gate holder and locking screws and screwdriver, as shown in FIG. 10B. The wound is then closed, completing the procedure.

I claim:

1. A spinal fusion system, comprising:
    a cage structure including a posterior wall and opposing lateral sidewalk defining a fillable volume;
    the cage structure having a convex, dome-shaped superior surface and a substantially flat interior surface when viewed from the side;
    a removable locking anterior gate, enabling the fillable volume to be packed with graft, biologic or other materials after the cage structure is inserted within an intervertebral space prior to the gate being closed and locked;
    the system including a plurality of the cage structures, each with an anterior height, a posterior height, and a locking gate;
    including cages wherein the anterior height is greater than the posterior height, resulting in structures that are trapezoidally shaped when viewed from the side; and
    including cages which are larger and more trapezoidally-pronounced as compared to other of the cages for L5-S1 spinal levels.

2. A spinal fusion system, comprising:
- a cage structure including a posterior wall and opposing lateral sidewalls defining a fillable volume;
- the cage structure having a convex, dome-shaped superior surface and a substantially flat interior surface when viewed from the side;
- a removable locking anterior gate, enabling the fillable volume to be packed with graft, biologic or other materials after the cage structure is inserted within an intervertebral space prior to the gate being closed and locked;
- the system including a plurality of the cage structures, each with an anterior height, a posterior height, and a locking gate;
- including cages wherein the anterior height is greater than the posterior height, resulting in structures that are trapezoidally shaped when viewed from the side; and
- including cages which are smaller and less trapezoidally pronounced as compared to other of the cages for the T and L2 spinal levels.

* * * * *

UNITED STATES PATENT AND TRADEMARK OFFICE
CERTIFICATE OF CORRECTION

PATENT NO. : 7,674,297 B2
APPLICATION NO. : 10/462498
DATED : March 9, 2010
INVENTOR(S) : Mark H. Falahee It is certified that error appears in the above-identified patent and that said Letters Patent is hereby corrected as shown below:

Column 4, line 34: After "L5 levels" insert --at 402--;

Column 4, line 34: After "Dilation" insert --206--;

Column 4, line 34: After "shown" replace "as" with --in--;

Column 4, line 35: Before "shown" insert --is--;

Column 4, line 35: After "9C" insert --at 208--;

Column 4, line 35: Replace "FIGS. 9D and" with --FIG. 9D.--;

Column 4, line 36: Delete "9E." (first occurrence);

Column 4, line 37: After "endplates" insert --410--;

Column 4, line 50: Replace "sidewalk" with --sidewall--; and

Column 5, line 5: Replace "haying" with --having--.

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,674,297 B2 | |
| APPLICATION NO. | : 10/462498 | |
| DATED | : March 9, 2010 | |
| INVENTOR(S) | : Falahee | |

It is certified that error appears in the above-identified patent and that said Letters Patent is hereby corrected as shown below:

Column 4, Line 52 reads, "surface and a substantially flat interior..." which should read, "surface and a substantially flat inferior..."

Column 5, Line 6 reads, "surface and a substantially flat interior..." which should read, "surface and a substantially flat inferior..."

Signed and Sealed this
Third Day of May, 2011

David J. Kappos
*Director of the United States Patent and Trademark Office*